United States Patent [19]
Todd et al.

[11] Patent Number: 4,534,765
[45] Date of Patent: Aug. 13, 1985

[54] MODULAR DRAINAGE APPARATUS HAVING EXCESS NEGATIVITY CONTROL

[75] Inventors: Edward P. Todd, Lexington, Ky.; Eugene E. Weilbacher, New Philadelphia, Ohio

[73] Assignee: Snyder Laboratories, Inc., Dover, Ohio

[21] Appl. No.: 386,252

[22] Filed: Jun. 8, 1982

[51] Int. Cl.$^3$ .............................................. A61M 1/00
[52] U.S. Cl. ................................................... 604/321
[58] Field of Search ............................... 604/317–321; 137/205

[56] References Cited

U.S. PATENT DOCUMENTS

| | | | |
|---|---|---|---|
| 3,847,152 | 11/1974 | Schachet | 604/321 |
| 4,289,158 | 9/1981 | Nehring | 137/205 |
| 4,439,190 | 3/1984 | Protzmann et al. | 604/319 |
| 4,455,141 | 6/1984 | Todd | 604/321 |

OTHER PUBLICATIONS

"Understanding Underwater Chest Drainage", Chesebrough-Ponds Inc.

Primary Examiner—Stephen C. Pellegrino
Assistant Examiner—J. L. Kruter
Attorney, Agent, or Firm—Frank C. Leach, Jr.

[57] ABSTRACT

A modular drainage apparatus has a plurality of preformed plastic bodies supported by a header. One of the bodies includes a collection chamber connected to the pleural cavity of a patient and connected to a first passage formed in the header. A second body includes a U-shaped liquid seal chamber having one end connected to the first passage and its other end connected to a second passage formed in the header. The second passage is connected to a vacuum pump, which creates a suction within the collection chamber through the liquid seal chamber. A third body includes a U-shaped chamber to regulate the negative pressure produced by the vacuum pump to a desired negative pressure. The second body also includes a second U-shaped chamber having one end connected to the atmosphere and its other end connected to the liquid seal chamber adjacent its connection to the first passage. By filling each leg of the second U-shaped chamber of the second body to a selected level with a liquid, the negative pressure in the collection chamber is maintained at a selected maximum above the pressure maintained in the collection chamber by the vacuum pump and regulated by the U-shaped chamber of the third body.

43 Claims, 21 Drawing Figures

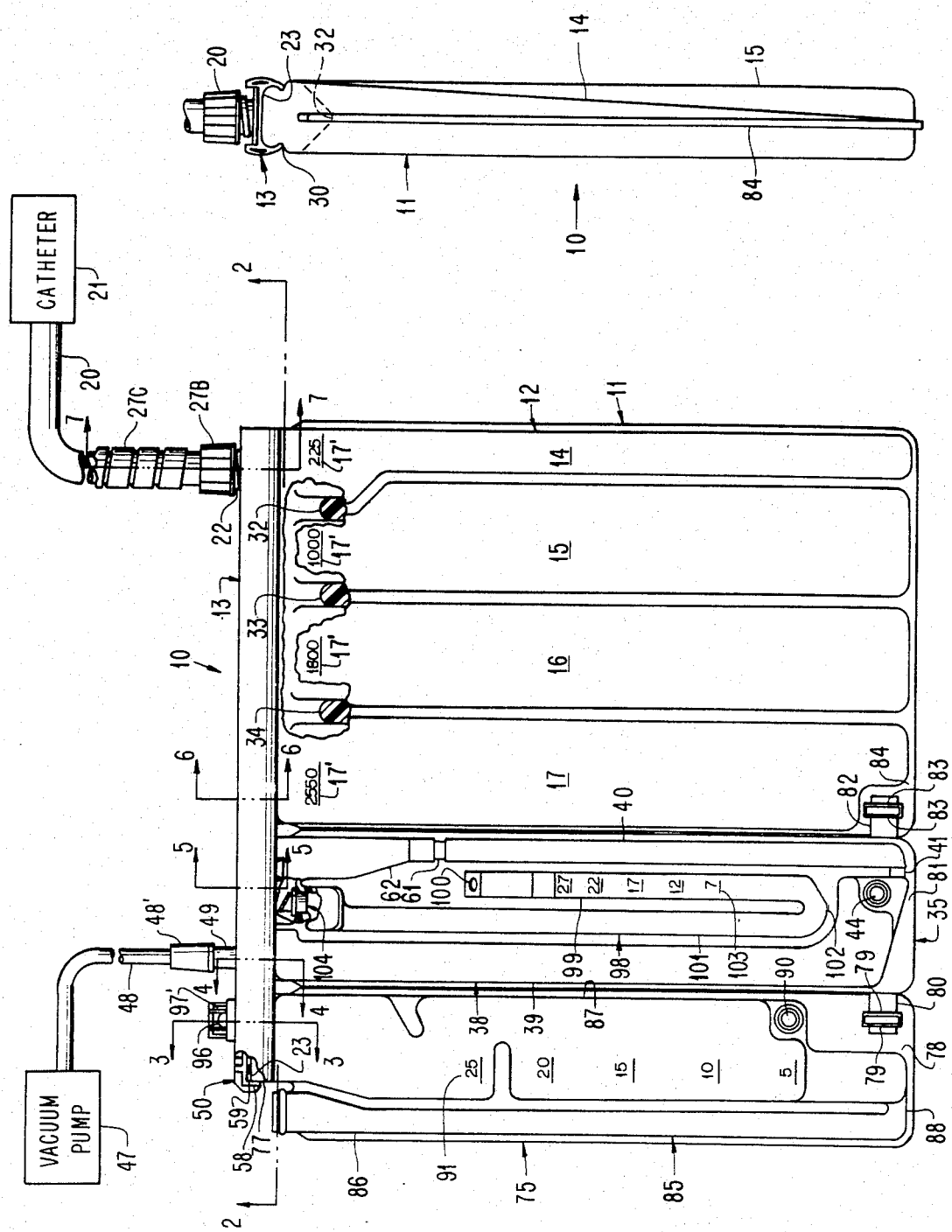

MODULAR DRAINAGE APPARATUS HAVING EXCESS NEGATIVITY CONTROL

This invention relates to a modular drainage apparatus and, more particularly, to a modular drainage apparatus for draining fluids from a pleural cavity of a body while controlling the negative pressure within the pleural cavity to a selected maximum.

In the copending patent application of Edward P. Todd for "Drainage Apparatus," Ser. No. 386,241, filed June 8, 1982, now U.S. Pat. No. 4,455,141 there is shown a drainage apparatus for draining fluids from a pleural cavity of a body while limiting the maximum negative pressure within the pleural cavity. The modular drainage apparatus of the present invention is an apparatus of the type shown and described in the aforesaid Todd application having an arrangement to prevent loss of liquid from the excess negativity chamber.

Various types of drainage apparatuses have been developed for use in draining fluids from the pleural cavity of a human being in a clean and aseptic environment. Examples of these drainage apparatuses are disclosed in U.S. Pat. No. 3,363,626 to Bidwell et al, U.S. Pat. No. 3,363,627 to Bidwell et al, U.S. Pat. No. 3,559,647 to Bidwell et al, U.S. Pat. No. 3,683,913 to Kurtz et al, U.S. Pat. No. 3,757,783 to Alley, U.S. Pat. No. 3,783,870 to Schachet, U.S. Pat. No. 3,853,128 to Kurtz et al, U.S. Pat. No. 3,924,624 to Schachet, U.S. Pat. No. 3,946,735 to DeWall, U.S. Pat. No. 4,195,633 to Nehring et al, and U.S. Pat. No. 4,289,158 to Nehring.

The drainage apparatus of each of the aforesaid patents discloses an arrangement for draining fluids from the pleural cavity of a human being into a collection chamber maintained at a negative pressure. While the apparatuses of most of the aforesaid patents are capable of controlling the negative pressure in the collection chamber, which receives the fluids from the pleural cavity of the human being, so that a minimum predetermined negative pressure exists within the collection chamber, none of the apparatuses of the aforesaid patents has any arrangement for limiting an increase in negative pressure in the pleural cavity of a human being to a selected maximum when such occurs as is accomplished by the apparatus of the aforesaid Todd application.

There are times when it is desired to increase the negative pressure within the pleural cavity of a human being for a short period of time. This is to cause break up of any blood clots in the pleural cavity, break up of any fibrin accumulation around the chest tube in the body, and break up of any materials collected within the tube leading from the pleural cavity of the human being to the collection chamber of the modular drainage apparatus. This increase in negative pressure in the pleural cavity can be accomplished through compressing and stripping the tube leading from the pleural cavity of the human being to the collection chamber of the modular drainage apparatus so as to produce a sudden increase in negative pressure while also causing the tube to be stripped of any materials therein so that they pass into the collection chamber in the modular drainage apparatus.

It is desired to be able to dissipate this excess negative pressure in the pleural cavity as soon as possible and within a relatively short period of time such as no more than three minutes, for example. If this excess negative pressure in the pleural cavity is not reduced within a relatively short period of time, this excess negative pressure in the pleural cavity can cause barotrauma to the lungs. This can result in an air leak in the lung or lungs exposed to this excess negative pressure to cause further medical complications of the person whose pleural cavity is connected to the collection chamber of the modular drainage apparatus.

One means of reducing the excess negative pressure in the pleural cavity would be to disconnect the tube, which is between the pleural cavity of the human being and the collection chamber of the modular drainage apparatus, to allow atmospheric air to enter the collection chamber. However, this air pressure could cause collapse of one or both of the lungs due to the transient evacuation of the negative pressure. Furthermore, this defeats the purpose of the modular drainage apparatus providing a clean and aseptic environment since the disconnection of the tube could result in contamination. Therefore, this disconnection of the tube is a totally unsatisfactory arrangement for reducing the excess negative pressure. Additionally, this disconnection of the tube would depend upon the attendant recognizing the time at which it is desired to reduce this excess negative pressure.

While the drainage apparatus of the aforesaid U.S. Pat. No. 3,683,913 to Kurtz et al includes a valve to permit development of a high negative pressure in the pleural cavity of a human being when the person is attempting to expand the lungs to make a strong respiratory effort to open a blockage in his or her bronchial tubes, for example, there is no way of relieving the increased negative pressure. That is, in the apparatus of the aforesaid U.S. Pat. No. 3,683,913 to Kurtz et al, the person, who is connected to the collection chamber of the drainage apparatus, must have a reduction in the negative pressure in the pleural cavity before the valve returns to its open position.

Thus, the drainage apparatus of the aforesaid U.S. Pat. No. 3,683,913 to Kurtz et al seems to increase the possibility of barotrauma in the lungs. This is because there is no means to dissipate the increased negative pressure in the pleural cavity; instead, it is maintained in the pleural cavity. Therefore, a prolonged exposure of the lungs to the excess negative pressure in the pleural cavity would appear to occur when using the drainage apparatus of the aforesaid U.S. Pat. No. 3,683,913 to Kurtz et al.

The modular drainage apparatus of the present invention satisfactorily solves the foregoing problem of allowing an increased negative pressure to be created within the pleural cavity of a person connected to the collection chamber of the modular drainage apparatus for a predetermined period of time with this period of time being sufficiently small so that the chance for barotrauma to the lungs of the person connected to the collection chamber of the modular drainage apparatus will be minimized. The modular drainage apparatus of the present invention limits the negative pressure in the pleural cavity to a predetermined or selected maximum above the selected negative pressure, which is produced within the collection chamber of the modular drainage apparatus by the combination of the vacuum pump and the pressure regulating chamber. Thus, the excess negative pressure in the pleural cavity of the person connected to the collection chamber of the modular drainage apparatus is limited so that the negative pressure does not become too large or exist for too long a period of time. This arrangement allows the negative pressure to be increased so that the tube from the pleural cavity to the collection chamber of the modular drainage apparatus can be stripped to produce a sudden increase in negative pressure in the pleural cavity to break up clots therein and to break up fibrin which have accumulated in or around the chest tube in the body.

However, the modular drainage apparatus of the present invention does not allow this excess negative pressure to persist for a period of time in which there can be damage to the lungs. Therefore, the modular drainage apparatus of the present invention not only enables the negative pressure in the pleural cavity to be increased when desired through stripping the tube, which connects the pleural cavity to the collection chamber of the modular drainage apparatus, but also insures that this negative pressure does not remain for an undesirable period of time.

Additionally, if the negative pressure in the pleural cavity of the person connected to the collection chamber of the modular drainage apparatus should increase for any reason, this excess negative pressure is dissipated by the arrangement used in the modular drainage apparatus of the present invention. Thus, constant monitoring of the patient is not necessary to ascertain if there is excess negative pressure in the patient's pleural cavity.

While the drainage apparatus of the aforesaid U.S. Pat. No. 3,363,627 to Bidwell et al discloses a reservoir to collect liquid to recognize when there has been an excess negative pressure in the pleural cavity of the person connected to the collection chamber of the drainage apparatus, this may not be recognized until damage has been done to the lungs of the patient. That is, the reservoir might not be inspected until the next morning as is mentioned in the aforesaid U.S. Pat. No. 3,363,627 to Bidwell et al. By this time, substantial damage may have been done to the lungs of the patient.

This problem is avoided by the modular drainage apparatus of the present invention. This is because the modular drainage apparatus of the present invention does not allow the negative pressure in the pleural cavity to remain above a predetermined or selected maximum above the negative pressure produced in the collection chamber of the modular drainage apparatus by the vacuum source beyond a predetermined period of time.

When an excess negative pressure exists in the pleural cavity of a patient connected to the collection chamber of the modular drainage apparatus of the present invention, the possiblity exists that the liquid in the excess negativity chamber could enter into the liquid seal chamber with which it is connected. The loss of a sufficient amount of the liquid from the excess negativity chamber to the liquid seal chamber during the time that there is an excess negative pressure in the pleural cavity of a patient connected to the collection chamber of the modular drainage apparatus of the present invention could result in insufficient liquid remaining within the excess negatavity chamber when the excess negative pressure ceases to exist.

The modular drainage apparatus of the present invention satisfactorily solves this problem through providing flow control vent means at the connection of the excess negativity chamber with the liquid seal chamber. This flow control vent means prevents liquid from flowing from the excess negativity chamber into the liquid seal chamber while still allowing air to flow therethrough to reduce the excess negative pressure in the pleural cavity of a patient connected to the collection chamber of the modular drainage apparatus of the present invention.

An object of this invention is to provide a modular drainage apparatus in which flow of liquid between an excess negativity chamber and a liquid seal chamber is prevented.

Another object of this invention is to provide a modular drainage apparatus in which loss of liquid from a liquid seal chamber is prevented.

Other objects of this invention will be readily perceived from the following description, claims, and drawings.

This invention relates to a modular drainage apparatus including three bodies supported by support means, which has two passage means. A first of the bodies has a pressure regulating chamber communicating with one of the passage means. A second of the bodies includes a liquid seal chamber adapted to have a selected quantity of liquid therein with the liquid seal chamber having one end communicating with the one passage means to communicate with the pressure regulating chamber of the first body and its other end communicating with the other of the passage means. A third of the bodies has a collection chamber, which has inlet means for connection to a pleural cavity of a body to receive fluids therefrom, communicating with the other passage means to communicate with the other end of the liquid seal chamber of the second body. The one passage means includes means to enable a negative pressure, which is controlled by the pressure regulating chamber of the first body, to be applied to the liquid seal chamber and the collection chamber and to remove gases from the fluids in the collection chamber to the liquid seal chamber. The second body also includes an excess negativity chamber having one end communicating with the other passage means and its other end communicating with the atmosphere and adapted to have a selected quantity of liquid therein to limit the negative pressure within the collection chamber to a selected maximum above the negative pressure controlled by the pressure regulating chamber.

This invention also relates to a modular drainage apparatus including three bodies with each body including at least one chamber having an upper wall and a groove on each side of the body adjacent at least the upper wall of the one chamber. Each of the bodies is supported by support means having a longitudinally extending wall and means for disposition within the groove in each of the bodies to cause each of the bodies to have the upper wall of at least the one chamber abut the longitudinally extending wall. The upper wall of the one chamber of each of the bodies has at least one opening therein communicating through an opening in the longitudinally extending wall of the support means with one of two passage means in the support means so that the one chamber of each of the bodies communicates with the one chamber of at least one other of the bodies. A first of the bodies has the one chamber communicating with one of the passage means through the one opening in the upper wall of the one chamber. A second of the bodies has two openings in the upper wall of the one chamber, which includes a liquid seal chamber adapted to have a selected quantity of liquid therein, with the one chamber of the second body communicating with the one passage means through one of the openings to communicate with the one chamber of the first body and the one chamber of the second body communicating with the other of the passage means remote from its communication with the one passage means through the other of the openings. A third of the bodies has the one chamber, which is a collection chamber having inlet means for connection to a pleural cavity of a body to receive fluids therefrom, communicating with the other passage means through the one opening in the upper wall of the one chamber to communicate with the one chamber of the second body. The one passage means includes means to enable a negative pressure, which is controlled by the one chamber of the first body, to be applied to the liquid seal chamber and the collection chamber and to remove gases from the fluids in the collection chamber to the liquid seal chamber. The second body also has an excess negativity chamber having one end communicating with the other passage means and its other end communicating with the atmosphere and adapted to have a selected quantity of liquid therein to limit the negative pressure within the collection chamber to a selected maximum above the negative pressure controlled by the one chamber of the first body.

The attached drawings illustrate preferred embodiments of the invention, in which:

FIG. 1 is a front elevational view, partly schematic, of the modular drainage apparatus of the present invention;

FIG. 1A is an end elevational view of the modular drainage apparatus of FIG. 1;

Figures 2, 5, 6:
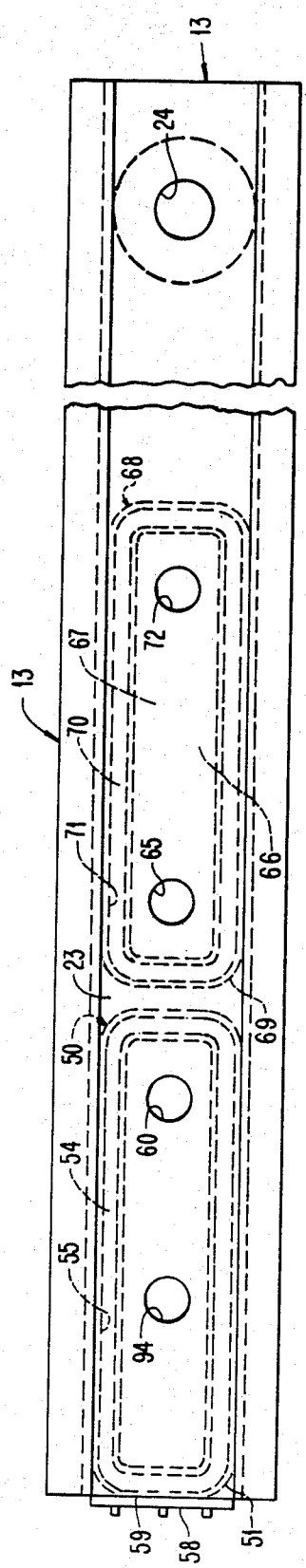
FIG. 2 is a bottom plan view of a header of the modular drainage apparatus of FIG. 1 and taken along line 2—2 of FIG. 1.
FIG. 5 is a fragmentary sectional view of the modular drainage apparatus of FIG. 1 taken along line 5—5 of FIG. 1 and showing the liquid seal chamber communicating with a second sealed chamber.
FIG. 6 is a fragmentary sectional view of the modular drainage apparatus of FIG. 1 taken along line 6—6 of FIG. 1 and showing the collection chamber communicating with the second sealed chamber.

Referring to the drawings and particularly FIG. 1, there is shown a drainage apparatus 10 for draining fluid from the pleural cavity of a patient. The drainage apparatus 10 has a modular configuration with this modular configuration being the invention of Eugene E. Weilbacher as claimed in his copending patent application for "Modular Apparatus," Ser. No. 386,242, filed June 8, 1982, now U.S. Pat. No. 4,465,483.

The drainage apparatus 10 includes a first transparent plastic body or unit 11 having a collection or trap chamber 12 for receiving fluids from the pleural cavity of the patient. The first body or unit 11 is supported by a header 13, which functions as support means for the body or unit 11, and is preferably a non-transparent plastic.

The collection chamber 12 is divided into four compartments 14, 15, 16, and 17. The compartment 14 is much smaller than each of the compartments 15, 16, and 17 so that it may be used as a special pediatric compartment to accurately measure the quantity of liquids in the fluids obtained from the pleural cavity of a child when the drainage apparatus 10 is used with a child so as to maximize the accuracy of the determination of fluid loss.

The compartment 14 holds 225 cc of liquids. The compartment 15 retains 775 cc of liquids. The compartment 16 holds 800 cc of liquids, and the compartment 17 retains 750 cc of liquids. Thus, the compartments 14–17 can hold a total volume of 2550 cc of liquids. Each of the compartments 14–17 has indicia 17' to indicate the total volume of liquids collected in the collection chamber 12.

Figure 7:
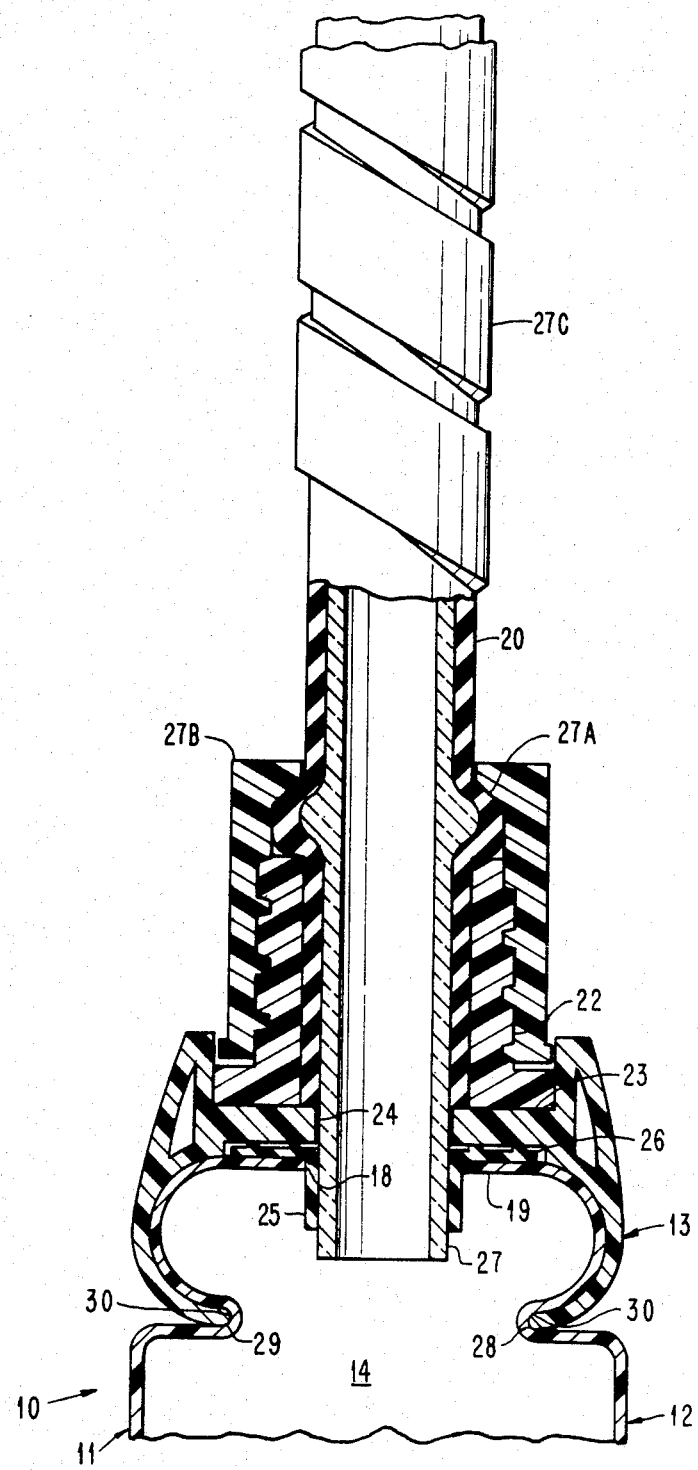
FIG. 7 is a fragmentary sectional view of the modular drainage apparatus of FIG. 1 taken along line 7—7 of FIG. 1 and showing the collection chamber communicating with a hose leading to the pleural cavity of a patient.

The collection chamber 12 has an inlet 18 (see FIG. 7) in its substantially horizontal upper wall 19 above the compartment 14, which is the pediatric compartment. Thus, the liquids from the fluids obtained from the pleural cavity of any patient connected to the drainage apparatus 10 are initially collected in the compartment 14.

The inlet 18 of the collection chamber 12 communicates with the pleural cavity of a patient through a flexible tube 20 (see FIG. 1). The tube 20 has one end connected to the pleural cavity of the patient through a catheter 21, for example, and its other end extending into a hollow fitting 22, which is fixed to the upper surface of a horizontally extending wall 23 (see FIG. 7) of the header 13 and has threads on its outer surface.

The horizontally extending wall 23, which extends for the length of the header 13, has a circular passage 24 extending therethrough and communicating with the inlet 18 in the upper wall 19 of the collection chamber 12. A gasket 25, which is formed of a suitable elastomeric material such as nitrile rubber, for example, is disposed within the inlet 18 and has an annular flange 26 abutting against the bottom surface of the wall 23 of the header 13 and surrounding the bottom end of the passage 24 in the wall 23 of the header 13 so as to form a seal therewith whereby the fluids from the pleural cavity of the patient will flow into the compartment 14 of the collection chamber 12.

The flexible tube 20 has a translucent plastic tube 27 disposed in its lower end and extending through the passage 24 in the wall 23 of the header 13 and the interior of the gasket 25 to communicate with the interior of the compartment 14. The extension of the tube 27 into the compartment 14 is controlled by a projection 27A on the flexible tube 20 abutting the upper surface of the fitting 22.

A threaded cap 27B, which has threads on its inner surface cooperating with the threads on the outer surface of the fitting 22, pushes the projection 27A into engagement with the upper surface of the fitting 22 to retain the flexible tube 20 within the hollow fitting 22. This also produces a seal to prevent any leakage of air into the compartment 14.

The outer surface of the portion of the tube 20 adjacent the upper end of the tube 27 has an element 27C, which is formed of a suitable translucent plastic, wrapped therearound and fitting firmly so as to not be mobile. The element 27C prevents any kinking of the flexible tube 20.

The header 13 has its support edges 28 and 29 disposed within slots or grooves 30 formed in the exterior of the upper end of the body 11 on opposite sides thereof to enable the header 13 to support the body 11. Thus, the annular flange 26 of the gasket 25 is held against the bottom surface of the horizontally extending wall 23 of the header 13 to form the seal between the passage 24 in the wall 23 and the inlet 18 in the upper wall 19 of the body 11.

As shown in FIG. 1, the upper end of the compartment 14 of the collection chamber 12 communicates with the upper end of the compartment 15 of the collection chamber 12 by a V-shaped channel or passage 32. Thus, when the compartment 14 becomes filled with liquids so that the compartment 14 has 225 cc of liquids therein, the liquids flow into the compartment 15 through the channel or passage 32.

The upper end of the compartment 15 of the collection chamber 12 communicates through a V-shaped channel or passage 33 with the upper end of the compartment 16. Accordingly, when the compartments 14 and 15 become filled with liquids so that the compartments 14 and 15 have a total of 1000 cc of liquids therein, the liquids enter the compartment 16 through the channel or passage 33.

The upper end of the compartment 16 of the collection chamber 12 communicates with the upper end of the compartment 17 of the collection chamber 12 through a V-shaped channel or passage 34. Therefore, when the compartment 16 becomes filled with liquids so that the compartments 14, 15, and 16 have a total of 1800 cc of liquids therein, the liquids flow into the compartment 17 through the channel or passage 34.

The header 13 supports a second body or unit 35 adjacent the first body 11. The second body 35 has a pair of slots or grooves 36 (see FIG. 5) formed in its exterior on opposite sides thereof adjacent its upper end to receive the edges 28 and 29 of the header 13.

Figure 14:
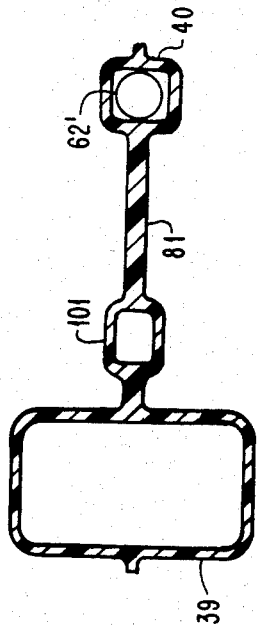
FIG. 14 is a sectional view of the body of FIG. 8 and taken along line 14—14 of FIG. 8.
Figure 15:
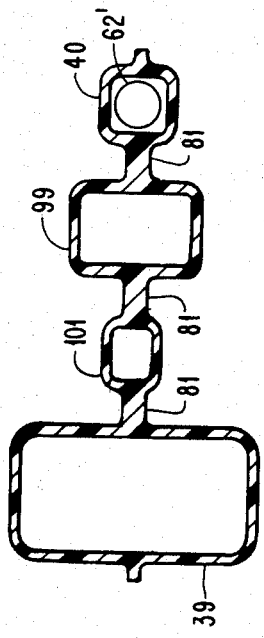
FIG. 15 is a sectional view of the body of FIG. 8 and taken along line 15—15 of FIG. 8.
Figure 16:
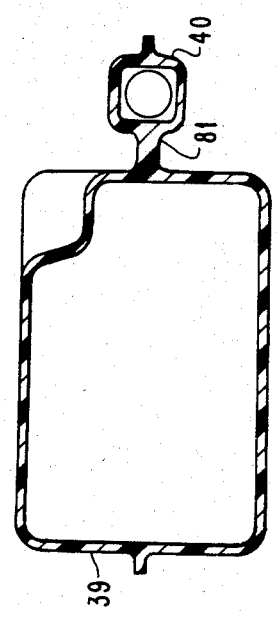
FIG. 16 is a sectional view of the body of FIG. 8 and taken along line 16—16 of FIG. 8.
Figure 11:
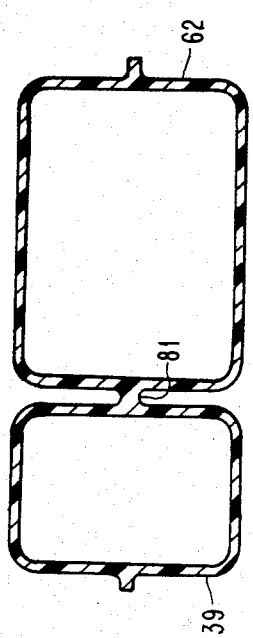
FIG. 11 is a sectional view of the body of FIG. 8 and taken along line 11—11 of FIG. 8.
Figure 12:
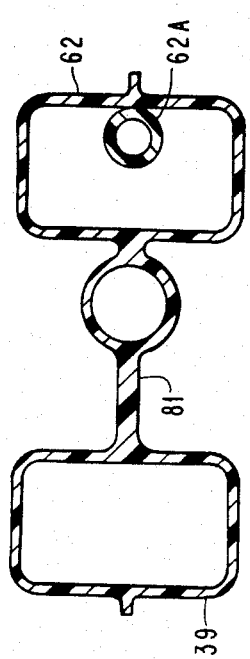
FIG. 12 is a sectional view of the body of FIG. 8 and taken along line 12—12 of FIG. 8.
Figure 13:
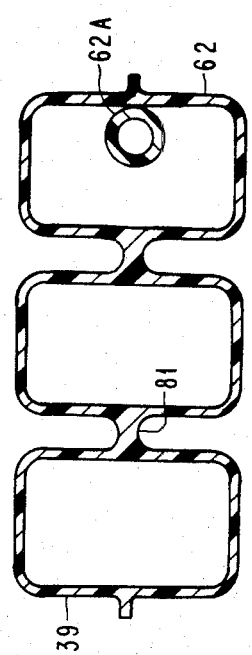
FIG. 13 is a sectional view of the body of FIG. 8 and taken along line 13—13 of FIG. 8.

The body 35 (see FIGS. 1 and 8) includes a liquid seal chamber 38. The liquid seal chamber 38 includes a first column 39 and a second column 40. The relationships of the cross sectional areas of the columns 39 and 40 are shown in FIGS. 14 to 16.

Figures 8, 9, 10:
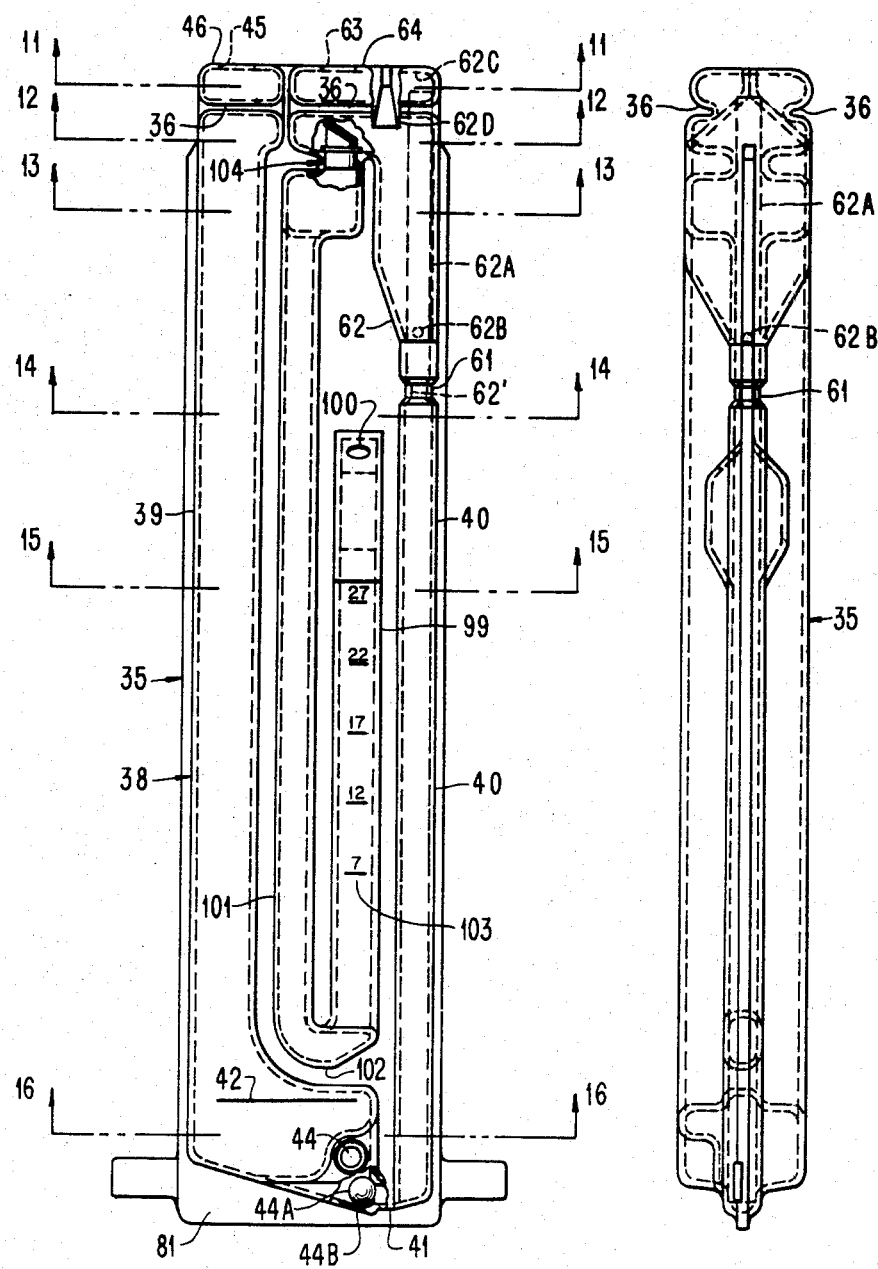
FIG. 8 is a front elevational view, partly in section, of one of the three bodies forming the modular drainage apparatus and including the arrangement for preventing excess negative pressure within the pleural cavity of a patient connected to the modular drainage apparatus.
FIG. 9 is an end elevational view of the body of FIG. 8.
FIG. 10 is a top plan view of the body of FIG. 8.

The columns 39 and 40 communicate with each other at their bottom ends through a passage 41 so that the liquid seal chamber 38 is substantially U-shaped. Liquid such as water, for example, spans the bottom of the two columns 39 and 40 and extends to a level line 42 as shown in FIG. 8. The liquid such as water, for example, is added to the columns 39 and 40 through a Luer valve 44 (see FIG. 1) in a wall of the liquid seal chamber 38 by adding water to the level line 42 (see FIG. 8).

A ball valve 44A is disposed in the lowermost portion of the first column 39 for cooperation with a valve seat 44B formed by the end of the passage 41 communicating with the bottom of the first column 39. The ball valve 44A does not completely prevent flow of liquid from the first column 39 to the second column 40 but retards flow so that there is no sudden evacuation of the liquid from the liquid seal chamber 38 to the collection chamber 12 (see FIG. 1). The ball valve 44A (see FIG. 8) also prevents large bubbles from flowing to the second column 40 to reduce the possibility of liquid flowing therewith.

Figure 4:
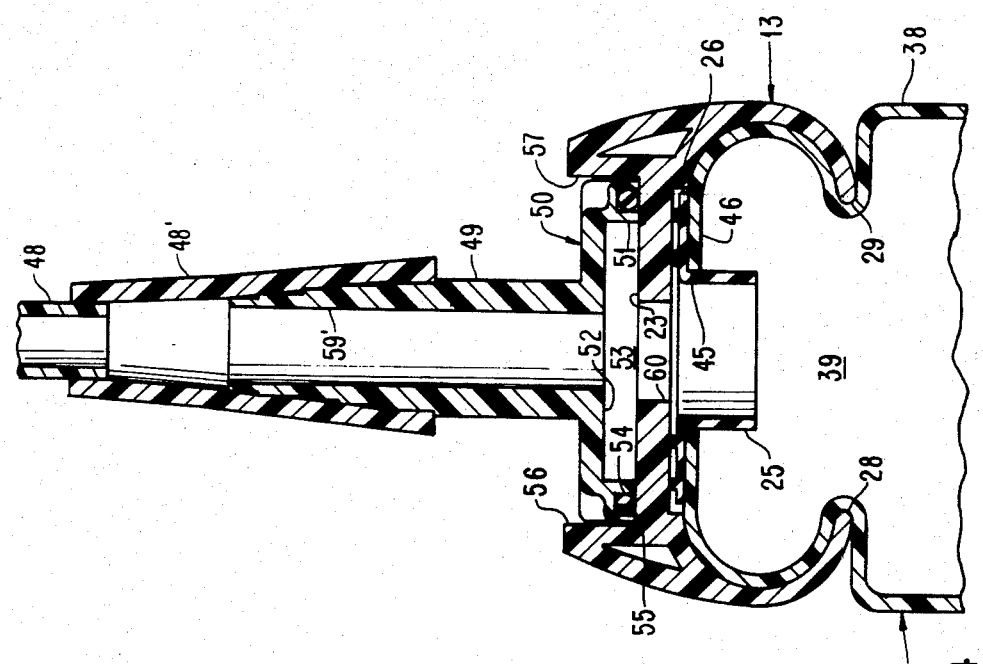
FIG. 4 is a fragmentary sectional view of the modular drainage apparatus of FIG. 1 taken along line 4—4 of FIG. 1 and showing the vacuum pump and the liquid seal chamber communicating with the same sealed chamber.

The first column 39 of the liquid seal chamber 38 has a circular inlet 45 (see FIG. 10) formed in its upper wall 46 for communication with a negative pressure source such as a vacuum pump 47 (see FIG. 1), for example, by a tube 48. The tube 48 is connected by a fitting 48' to a tapered and stepped hollow connector 49, which is formed integral with a manifold plate 50 (see FIGS. 2 and 4).

The manifold plate 50 is supported on the upper surface of the wall 23 of the header 13 and is fixed thereto by any suitable adhesive or bonding means. The manifold plate 50 has a peripheral projection 51 (see FIG. 4) extending downwardly to space a horizontally extending wall 52 of the manifold plate 50 from the upper surface of the wall 23 of the header 13 to form a chamber 53 therebetween. A sealing ring 54 is supported in a peripheral groove 55 in the peripheral projection 51 of the manifold plate 50 to form a seal with the upper surface of the wall 23 of the header 13.

The position of the manifold plate 50 on the header 13 is controlled by disposing the manifold plate 50 between a pair of upstanding walls 56 and 57 of the header 13. The longitudinal position of the manifold plate 50 is controlled by a flange 58 (see FIGS. 1 and 2) on one end of the manifold plate 50 bearing against an end 59 (see FIG. 2) of the wall 23.

As a result, the hollow connector 49 (see FIG. 4) has its passage 59' aligned with a circular passage 60 extending through the wall 23 of the header 13. The passage 60 communicates with the inlet 45 in the upper wall 46 of the first column 39 of the liquid seal chamber 38. The inlet 45 has one of the gaskets 25 disposed therein to form a seal with the passage 60 in the wall 23 of the header 13. Accordingly, the vacuum pump 47 (see FIG. 1 exerts a negative pressure within the chamber 53 (see FIG. 4) and the first column 39 (see FIGS. 1 and 8) of the liquid seal chamber 38.

The second column 40 of the liquid seal chamber 38 has its upper end 61 terminating in the lower end of a reservoir 62 through a reduced circular opening 62' (see FIG. 8) to reduce the rate of liquid flowing therethrough. The reservoir 62 has a vertically disposed bypass tube 62A extending upwardly therein from the reduced circular opening 62'. The tube 62A has holes 62B adjacent its lower end and is open at its upper end to provide communication from the interior of the tube 62A to the interior of the reservoir 62.

This structure prevents loss of any of the liquid from the liquid seal chamber 38 through the reservoir 62 to the collection chamber 12 (see FIG. 1), which is in communication with the reservoir 62 as will be explained hereinafter, when a patient gasps strongly. If a sufficient quantity of the liquid in the liquid seal chamber 38 were removed therefrom by the patient gasping strongly, atmospheric pressure could enter the pleural cavity of the patient if the vacuum pump 47 were disconnected.

When a patient gasps strongly to create a relatively high negative pressure within the patient's pleural cavity, liquid is initially rapidly drawn up the second column 40 (see FIG. 8) of the liquid seal chamber 38 and into the reservoir 62 through the holes 62B and the open upper end of the tube 62A. This rapid and sufficiently higher negativity within the pleural cavity of the patient transfers the liquid in the liquid seal chamber 38 into the reservoir 62.

However, the open upper end of the tube 62A is not blocked by the liquid sucked into the reservoir 62. As a result, air and liquid can flow through the open upper end of the tube 62A into the reservoir 62 for transmittal of air through the collection chamber 12 (see FIG. 1) to the pleural cavity of the patient. When the flow of air up the tube 62A (see FIG. 8) ceases, the liquid in the reservoir 62 immediately drains therefrom through the holes 62B in the tube 62A and down the second column 40 of the liquid seal chamber 38 to again establish the liquid seal in the liquid seal chamber 38. Thus, no liquid is lost from the liquid seal chamber 38.

It should be understood that liquid also passes through the open upper end of the tube 62A and engages a substantially horizontal wall 62C of the reservoir 62. This liquid is retained within the reservoir 62 by a substantially vertical wall 62D so that none of the liquid can escape through an opening 63 (see FIG. 10) in upper wall 64 of the reservoir 62.

The opening 63 communicates with a circular passage 65 (see FIG. 5) extending through the wall 23 of the header 13. The opening 63 has one of the gaskets 25 disposed therein to form a seal between the opening 63 and the passage 65.

The passage 65 in the wall 23 of the header 13 communicates with a chamber 66, which is formed between the wall 23 and a horizontally extending wall 67 of a manifold plate 68. The manifold plate 68 is secured to the wall 23 in the same manner as the manifold plate 50.

The manifold plate 68 has a peripheral projection 69 bearing against the upper surface of the wall 23 to space the wall 67 of the manifold plate 68 therefrom. The peripheral projection 69 has a sealing ring 70 mounted in a peripheral groove 71 in the peripheral projection 69 to seal the chamber 66. The manifold plate 68 is longitudinally positioned on the upper surface of the wall 23 of the header 13 so that the sealed chamber 66 also communicates with a circular passage 72 (see FIG. 6) extending through the wall 23. Thus, the passages 65 (see FIG. 5) and 72 (see FIG. 6) communicate with each other through the sealed chamber 66 so that the sealed chamber 66 functions as passage or communicating means.

The passage 72 is aligned with a circular outlet opening 73 in the upper wall 19 of the collection chamber 12. The outlet opening 73 has one of the gaskets 25 mounted therein to form a seal between the outlet opening 73 and the passage 72. Therefore, the reservoir 62 (see FIG. 1) communicates with the collection chamber 12 above the compartment 17 via the sealed chamber 66 (see FIG. 6).

Thus, the second column 40 (see FIG. 1) of the liquid seal chamber 38 is in communication with the collection chamber 12. Accordingly, any vacuum produced in the liquid seal chamber 38 by the vacuum pump 47 and regulated in a manner to be hereinafter described is created in the collection chamber 12 so that this same negative pressure exists within the pleural cavity of the patient connected to the collection chamber 12 of the drainage apparatus 10 by the tube 20.

A third body or unit 75 also is supported on the header 13. The body 75 has slots or grooves 76 (see FIG. 3) adjacent its upper end on its exterior to receive the edges 28 and 29 of the header 13. The body 75 has an end portion 77 (see FIG. 1) abutting the flange 58 of the manifold plate 50 (see FIG. 2), which is fixed to the header 13, to position the body 75 (see FIG. 1) on the header 13.

The third body 75 has a small portion of the lower end of its common connecting wall 78 punched or pushed out to form a pair of slots 79 to receive a tab 80 integrally formed on the lower end of a common connecting wall 81 of the second body 35. The reception of the tab 80 in the slots 79 joins the bodies 35 and 75 to each other at their lower ends with the adjacent edges of the walls 78 and 81 abutting.

The common connecting wall 81 of the second body 35 has a second tab 82 formed integral therewith on its lower end on the opposite end from the tab 80. The second tab 82 is disposed within slots 83, which are formed by punching or pushing out a small portion of a common connecting wall 84 of the first body 11. The disposition of the second tab 82 in the slots 83 joins the bodies 11 and 35 to each other at their lower ends with the walls 81 and 84 abutting.

It should be understood that the bodies 11, 35, and 75 are connected at their upper ends to the header 13 through the edges 28 (see FIG. 7) and 29 of the header 13 being disposed in the grooves 30, 36 (see FIG. 5), and 76 (see FIG. 3) in the bodies 11 (see FIG. 1), 35, and 75, respectively. The bodies 11, 35, and 75 are retained in position on the header 13 through the end portion 77 of the body 75 abutting the flange 58 of the manifold plate 50 (see FIG. 2) and the tube 27 (see FIG. 7) being disposed in the inlet 18 of the upper wall 19 of the first body 11. Thus, removal of the tube 27 enables easy replacement of the first body 11 when it is desired to replace the collection chamber 12.

The third body 75 (see FIG. 1) has a pressure regulating chamber 85, which controls the negative pressure applied by the vacuum pump 47 to the collection chamber 12. The pressure regulating chamber 85 includes a first column 86, which has its upper end open to communicate with the atmosphere, and a second column 87, which has a substantially larger cross sectional area than the first column 86. A passage 88 connects the bottom ends of the columns 86 and 87 to each other so that the pressure regulating chamber 85 is substantially U-shaped.

A liquid such as water, for example, is supplied to the passage 88 through a Luer valve 90 in the wall of the pressure regulating chamber 85 and spans the bottoms of the columns 86 and 87. The height of the liquid in the second column 87 controls the negative pressure produced by the vacuum pump 47 in the collection chamber 12. The second column 87 has indicia 91 thereon to indicate the level at which the liquid is to be disposed in the second column 87 to have the desired negative pressure produced in the collection chamber 12 by the vacuum pump 47.

The second column 87 has a circular outlet opening 92 (see FIG. 3) in its upper wall 93 in alignment with a circular passage 94 extending through the wall 23 of the header 13. The outlet opening 92 has one of the gaskets 25 disposed therein to form a seal between the opening 92 and the passage 94.

The passage 94 in the wall 23 of the header 13 communicates with the chamber 53. As previously mentioned, the chamber 53 has the vacuum pump 47 (see FIG. 1) connected thereto in addition to having the first column 39 of the liquid seal chamber 38 communicating therewith. Thus, the chamber 53 (see FIG. 3) functions as passage or communicating means.

Accordingly, when the vacuum pump 47 (see FIG. 1) is producing a negative pressure in the collection chamber 12, atmospheric air flows through the liquid spanning the bottom ends of the columns 86 and 87 of the pressure regulating chamber 85 to the chamber 53 (see FIG. 3) to insure that the vacuum pump 47 (see FIG. 1) does not create a negative pressure beyond that selected. Thus, the level of the liquid in the second column 87 controls the selected negative pressure.

The wall 52 (see FIG. 3) of the manifold plate 50 has a circular outlet opening 95 communicating with the atmosphere. The outlet opening 95 is normally closed by a ball check valve 96, which is disposed within a cage 97 having a plurality of openings 97'. The cage 97 is secured to an annular projection 97A on the wall 52 of the manifold plate 50 by any suitable adhesive or bonding means.

Figure 3:
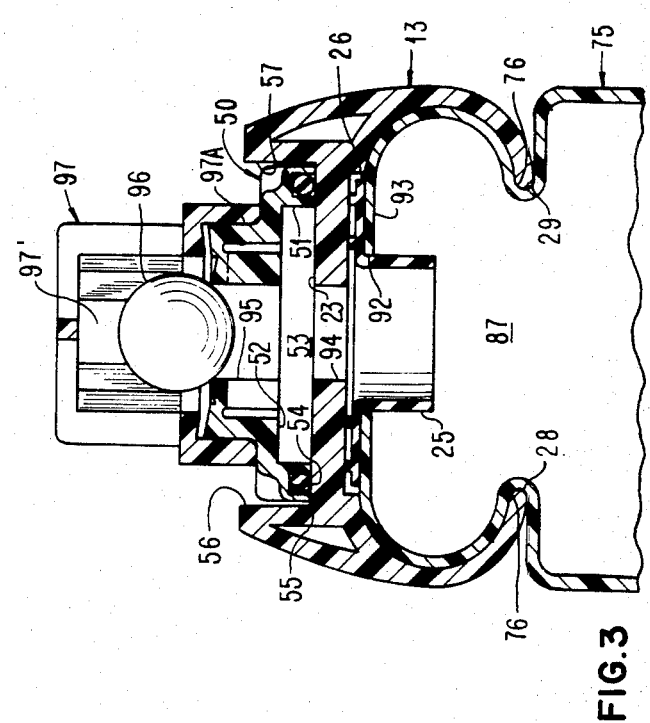
FIG. 3 is a fragmentary sectional view of the modular drainage apparatus of FIG. 1 taken along line 3—3 of FIG. 1 and showing the positive pressure relief valve and the pressure regulating chamber communicating with the same sealed chamber.

Accordingly, if the pressure in the collection chamber 12 (see FIG. 1) increases beyond atmospheric pressure and the pressure necessary to cross the liquid seal chamber 38, this increased pressure is vented through the liquid seal chamber 38 to the chamber 53 (see FIG. 3). This increased positive pressure is then vented to the atmosphere by the ball check valve 96 moving to an open position.

The body 35 (see FIG. 1) has an excess negativity chamber 98 formed therein. The excess negativity chamber 98 is utilized to limit the excess negative pressure in the collection chamber 12 and the pleural cavity of the patient connected to the tube 20 to a predetermined or selected maximum negative pressure greater than the negative pressure produced in the collection chamber 12 by the vacuum pump 47 in conjunction with the pressure regulating chamber 85 in a predetermined period of time. The selected maximum negative pressure is preferably two centimeters of water greater than the pressure selected in the pressure regulating chamber 85 with the predetermined period of time being preferably no more than three minutes.

The excess negativity chamber 98 is a U-shaped tube having a first leg or column 99 with its upper end communicating with the atmosphere through an opening 100 and a second leg or column 101 with its upper end communicating with the reservoir 62. The bottom ends of the legs or columns 99 and 101 are connected by a passage 102. A liquid, such as water, for example, is supplied through the opening 100 to span the bottom ends of the legs or columns 99 and 101.

The leg or column 99 has indicia 103 thereon to indicate the level to which the liquid is to be disposed in the leg or column 99. This level is selected in conjunction with the level of the liquid in the second column 87 of the pressure regulating chamber 85 to determine the selected maximum excess negative pressure. For example, if the second column 87 of the pressure regulating chamber 85 is set at twenty-five centimeters of water, then the column 99 is filled to twenty-seven centimeters of water.

Figure 18:
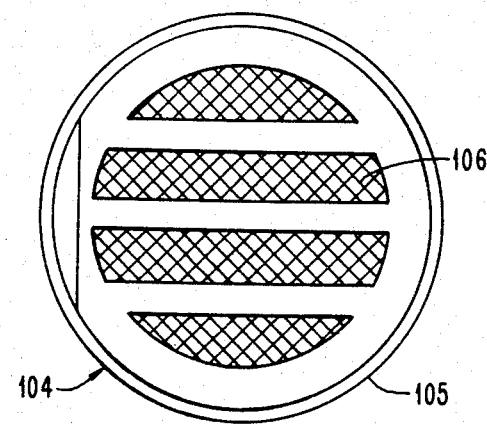
FIG. 18 is a top plan view of the flow control vent means of FIG. 17.
Figure 17:
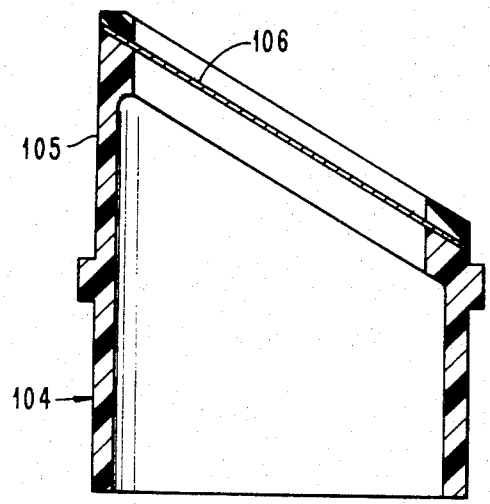
FIG. 17 is a sectional view of a flow control vent means used in controlling the excess negative pressure.

The upper end of the second leg or column 101 communicates with the reservoir 62 through flow control vent means 104 to the reservoir 62. As shown in FIGS. 17 and 18, the flow control vent means 104 includes a body 105, which is formed of a suitable plastic, having a filter 106 supported therein and through which the second leg or column 101 (see FIGS. 1 and 8) of the excess negativity chamber 98 communicates with the reservoir 62.

The material of the filter 106 (see FIGS. 17 and 18) is any suitable material capable of preventing the flow of liquid while allowing the flow of gas therethrough at a desired flow rate so as to function as a liquid check valve. Suitable examples of the material of the filter 106 of the flow control vent means 104 when the liquid is water are sold by Gelman Sciences, Ann Arbor, Mich. under the trademarks Acropor and Versapor.

Accordingly, the flow control vent means 104 prevents the liquid within the excess negativity chamber 98 (see FIG. 1) from flowing to the collection chamber 12 when there is a relatively high negative pressure existing in the pleural cavity of the patient connected to the collection chamber 12 through the tube 20 while still allowing flow of air at a selected flow rate in accordance with the porosity of the material of the filter 106 (see FIGS. 17 and 18) with this flow rate determining the period of time required to limit the excess negative pressure to the selected maximum.

It should be understood that the flow control vent means 104 results in the reduction of excess negativity by air flow through the excess negativity chamber 98 (see FIG. 8) being relatively slow so as not to be able to compensate for the strong gasp of a patient to avoid the possible loss of the liquid from the liquid seal chamber 38. Accordingly, the rate and mechanism of a patient's gasp are such that the excess negativity chamber 98 and the flow control vent means 104 could not always function in time to prevent the loss of liquid from the liquid seal chamber 38 without the bypass tube 62A.

Considering the operation of the drainage apparatus 10 (see FIG. 1) with the tube 20 connected to the pleural cavity of the patient and the vacuum pump 47 connected to the liquid seal chamber 38, the vacuum pump 47 produces a desired negative pressure in the collection chamber 12 in accordance with the height of the liquid in the second column 87 of the pressure regulating chamber 85. For example, the negative pressure could be twenty-five centimeters of water.

If the negative pressure in the pleural cavity of the patient increases beyond that produced by the vauum pump 47 in conjunction with the pressure regulating chamber 85, any increase in this negative pressure beyond the predetermined or selected maximum, as determined by the level of the liquid in the first leg or column 99 of the excess negativity chamber 98, results in atmospheric air flowing from the opening 100 through the liquid in the excess negativity chamber 98 into the collection chamber 12. Thus, the increase in the negative pressure in the pleural cavity of the patient connected to the tube 20 is limited. The flow rate of the air is controlled by the porosity of the material of the filter 106 (see FIGS. 17 and 18) of the flow control vent means 104.

It should be understood that limiting the excess negative pressure in the pleural cavity is the invention of Edward P. Todd and is shown, described, and claimed in the aforesaid copending Todd patent application.

Figure 19:
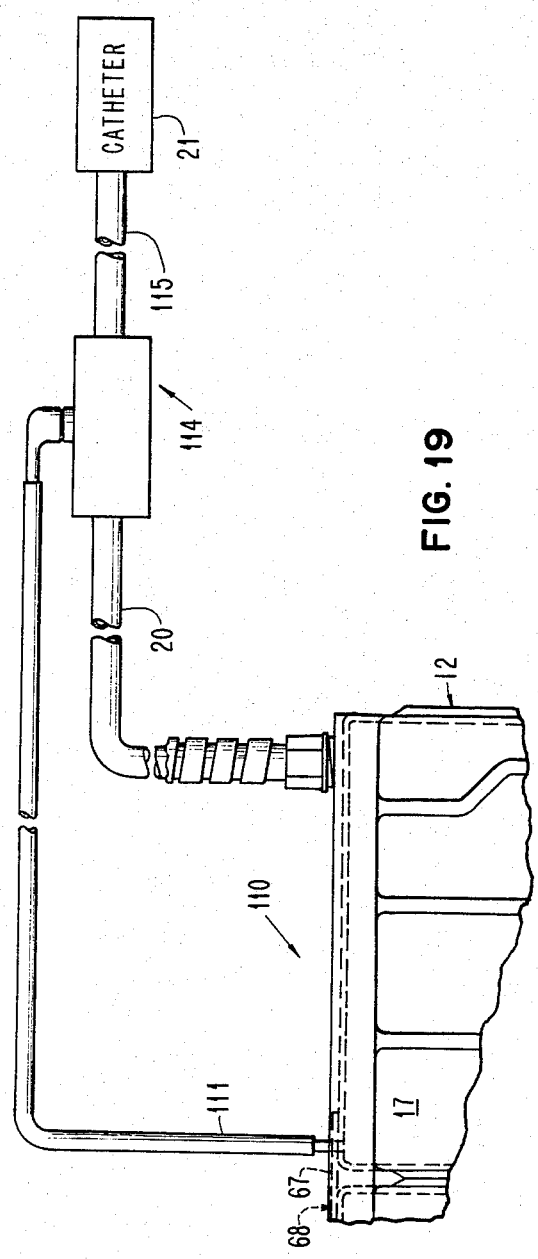
FIG. 19 is a fragmentary front elevational view of another form of the modular drainage apparatus of the present invention.

Referring to FIG. 19, there is shown a drainage apparatus 110, which is the same as the drainage apparatus 10 of FIG. 1 except as modified. The drainage apparatus 110 has one end of a flexible tube 111 communicating through an opening (not shown) in the horizontally extending wall 67 of the manifold plate 68 with the compartment 17 of the collection chamber 12. The opening (not shown) in the horizontally extending wall 67 of the manifold plate 68 is in vertical alignment with the passage 72 (see FIG. 6) extending through the wall 23 of the header 13.

Figure 20:
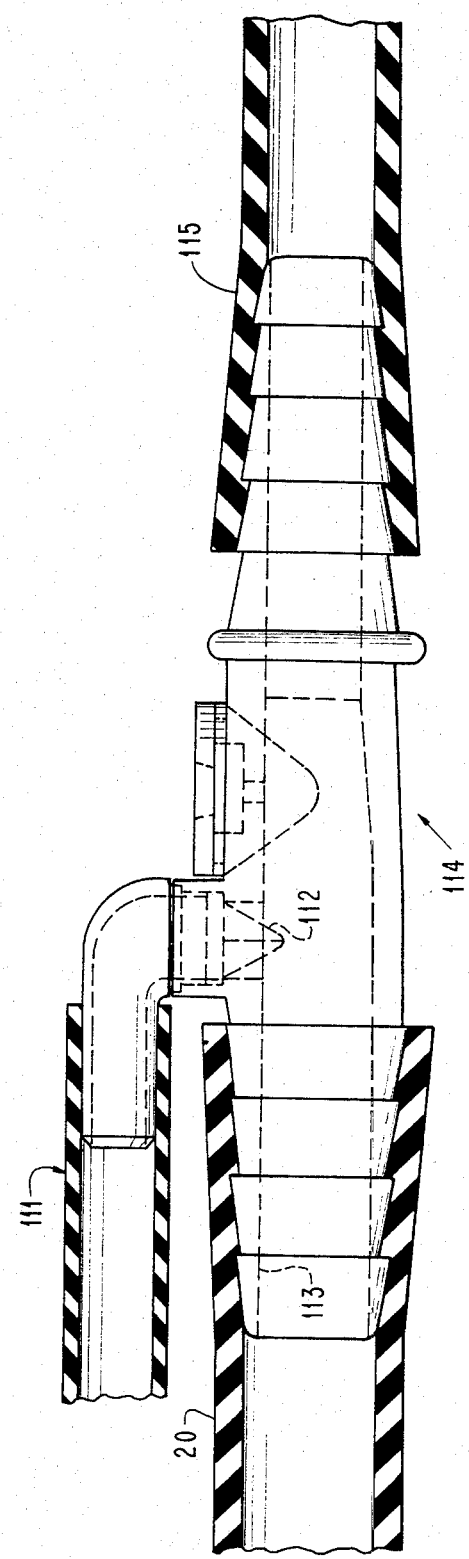
FIG. 20 is an elevational view of a connector used in connecting the modular drainage apparatus of FIG. 19 to the patient and showing the tubes in section.

The flexible tube 111 (see FIG. 19) has its other end connected through a check valve 112 (see FIG. 20), which may be a duck bill valve, with a passage 113 in a tubular connector 114. The tubular connector 114 is interposed between the tube 20 (see FIG. 19) and the catheter 21 so that a flexible tube 115 extends between the catheter 21 and the connector 114.

The arrangement enables the vacuum within the collection chamber 12 to be applied to the passage 113 (see FIG. 20) in the connector 114 whenever the pressure in the passage 113 decreases below that in the collection chamber 12 (see FIG. 19). Thus, increases in the negative pressure in the pleural cavity of the patient beyond the selected negative pressure within the collection chamber 12 are quickly reduced.

However, to break up any blood clots in the pleural cavity and any fibrin accomulation around the chest tube in the body, it is necessary to create a relatively high negative pressure such as a vacuum exceeding 400 mm Hg, for example, for a short period of time within the pleural cavity of the patient connected to the catheter 21. With the flexible tube 115 disposed between the catheter 21 and the connector 114, this relatively high negative pressure can be created within the pleural cavity of the patient by occluding the tube 115 from adjacent the catheter 21 downwardly to the connector 114. The check valve 112 (see FIG. 20) is located so that it does not prevent creation of the relatively high negative pressure by occlusion, which is produced by pinching the tube 115, of the tube 115.

The occluding of the tube 115 also causes stripping of the tube 115. This removes any fluids or clots accumulated therein to cause these to flow into the passage 113 in the connector 114 and then into the tube 20 by gravity.

Since this relatively high vacuum within the tube 115 could possibly draw the lung into the opening of the catheter 21 (see FIG. 19) because the interior of the lung is essentially at atmospheric pressure, it is desired to dissipate this relatively high negative pressure as soon as possible after stripping of the tube 115 is completed. The location of the check valve 112 (see FIG. 20) enables this relatively high negative pressure to be reduced rather quickly after the tube 115 is stripped because the pressure in the tube 115 equilibrates with the pressure in the collection chamber 12 (see FIG. 19). Residual negativity is then completely eliminated by the excess negativity chamber 98 (see FIG. 1).

Furthermore, if the occlusion is not maintained for the full length of the tube 115 (see FIG. 20) during stripping, the relatively high vacuum, which has been created behind the occlusion, would draw fluid back up the tube 20. However, because of the tube 111 providing communication from the collection chamber 12 (see FIG. 19) to the passage 113 (see FIG. 20) in the connector 114, this relatively high vacuum is quickly dissipated so that there is no relatively high vacuum to draw the fluid back up the tube 20.

The fluids passing through the passage 113 in the connector 114 from the tube 115 cannot enter the flexible tube 111 because of the check valve 112. Therefore, the effectiveness of the system cannot be reduced since fluid cannot enter the flexible tube 111.

After the tube 115 has been stripped, it is necessary to strip the tube 20 to remove any fluids and clots therein to the collection chamber 12 (see FIG. 19). These fluids and clots pass into the tube 20 from stripping of the tube 115.

When the tube 20 is stripped to remove any fluids and clots therein, there is no creation of any negative pressure by the occlusion created through pinching the tube 20. This is because the occlusion in the tube 20 cannot produce a higher negative pressure behind it than the negative pressure in the collection chamber 12 since the tube 111 provides communication betwen the collection chamber 12 and the passage 113 (see FIG. 20) in the connector 114. Thus, the tube 20 (see FIG. 19) is cleaned without creating a negative pressure.

If the tube 20 should ever be partially blocked by fluids, the pressure in the collection chamber 12 can still be commmunicated to the tube 115 through the tube 111. Thus, with the connector 114, fluid accumulation in the tube 20 does not affect the negative pressure in the plueral cavity.

If the modular drainage apparatus 110 is used with a patient having an air leak but no heart difficulty, then the tube 115 can be eliminated and the connector 114 connected to the catheter 21 by a very short tube. This is because there would be no requirement to produce a very high negative pressure within the pleural cavity of the patient to break up any blood clots in the pleural cavity or any fibrin accumulation around the chest tube in the body since the air leak will usually produce this.

An advantage of this invention is that there is no possible loss of liquid from the excess negativity chamber when an excess negative pressure exists in the pleural cavity of a person connected to the modular drainage apparatus. Another advantage of this invention is that there is no possible loss of liquid from the liquid seal chamber when the person connected to the modular drainage apparatus gasps strongly to create an excess negative pressure.

For purposes of exemplification, particular embodiments of the invention have been shown and described according to the best present understanding thereof. However, it will be apparent that changes and modifications in the arrangement and construction of the parts thereof may be resorted to without departing from the spirit and scope of the invention.

We claim:

1. A modular drainage apparatus including:
three bodies;
support means to support each of said bodies;
said support means having two passage means;

a first of said bodies having a pressure regulating chamber communicating with one of said passage means;

a second of said bodies including a liquid seal chamber adapted to have a selected quantity of liquid therein, said liquid seal chamber having one end communicating with said one passage means to communicate with said pressure regulating chamber of said first body and said liquid seal chamber having its other end communicating with the other of said passage means;

a third of said bodies having a collection chamber communicating with said other passage means to communicate with said other end of said liquid seal chamber of said second body;

said collection chamber having inlet means for connection to a pleural cavity of a body to receive fluids therefrom;

said one passage means including means to enable a negative pressure to be applied to said liquid seal chamber and said collection chamber and to remove gases from the fluids in said collection chamber to said liquid seal chamber;

said pressure regulating chamber of said first body controlling the negative pressure produced in said liquid seal chamber and said collection chamber;

and said second body including an excess negativity chamber having one end communicating with said other passage means and its other end continuously open and communicating with the atmosphere and adapted to have a selected quantity of liquid therein to limit the negative pressure within said collection chamber to a selected maximum above the negative pressure controlled by said pressure regulating chamber.

2. The modular drainage apparatus according to claim 1 in which:

said pressure regulating chamber of said first body is a U-shaped regulating chamber having one end exposed to the atmosphere and its other end connected to said one passage means;

and said U-shaped regulating chamber is adapted to have a selected quantity of liquid therein to control the negative pressure produced in said liquid seal chamber and said collection chamber.

3. The modular drainage apparatus according to claim 2 including means to prevent the flow of liquid from said one end of said excess negativity chamber while allowing air to flow through said excess negativity chamber to reduce the negative pressure in said collection chamber.

4. The modular drainage apparatus according to claim 3 in which:

said second body includes a reservoir between said other passage means and said liquid seal chamber;

communication means provides communication between said reservoir and said liquid seal chamber;

said reservoir communicates with said other passage means;

said reservoir provides communication between said excess negativity chamber and said liquid seal chamber and between said excess negativity chamber and said other passage means;

and said communication means includes means to prevent the flow of liquid from said liquid seal chamber through said reservoir to said other passage means.

5. The modular drainage apparatus according to claim 4 in which said communication means includes:

a vertically disposed tube within said reservoir having its lower end communicating with said liquid seal chamber and its upper end communicating with said reservoir;

and said tube having a set of holes adjacent its lower end to provide communication between the interior of said tube and said reservoir.

6. The modular drainage apparatus according to claim 2 in which:

said second body includes a reservoir between said other passage means and said liquid seal chamber;

communication means provides communication between said reservoir and said liquid seal chamber;

said reservoir communicates with said other passage means;

said reservoir provides communication between said excess negativity chamber and said liquid seal chamber and between said excess negativity chamber and said other passage means;

and said communication means includes means to prevent the flow of liquid from said liquid seal chamber through said reservoir to said other passage means.

7. The modular drainage apparatus according to claim 6 in which said communication means includes:

a vertically disposed tube within said reservoir having its lower end communicating with said liquid seal chamber and its upper end communicating with said reservoir;

and said tube having a set of holes adjacent its lower end to provide communication between the interior of said tube and said reservoir.

8. The modular drainage apparatus according to claim 1 including means to prevent the flow of liquid from said one end of said excess negativity chamber while allowing air to flow through said excess negativity chamber to reduce the negative pressure in said collection chamber.

9. The modular drainage apparatus according to claim 8 in which:

said second body includes a reservoir between said other passage means and said liquid seal chamber;

communication means provides communication between said reservoir and said liquid seal chamber;

said reservoir communicates with said other passage means;

said reservoir provides communication between said excess negativity chamber and said liquid seal chamber and between said excess negativity chamber and said other passage means;

and said communication means includes means to prevent the flow of liquid from said liquid seal chamber through said reservoir to said other passage means.

10. The modular drainage apparatus according to claim 9 in which said communication means includes:

a vertically disposed tube within said reservoir having its lower end communicating with said liquid seal chamber and its upper end communicating with said reservoir;

and said tube having a set of holes adjacent its lower end to provide communication between the interior of said tube and said reservoir.

11. The modular drainage apparatus according to claim 1 in which:

said second body includes a reservoir between said other passage means and said liquid seal chamber;

communication means provides communication between said reservoir and said liquid seal chamber;

said reservoir communicates with said other passage means;

said reservoir provides communication between said excess negativity chamber and said liquid seal chamber and between said excess negativity chamber and said other passage means;

and said communication means includes means to prevent the flow of liquid from said liquid seal chamber through said reservoir to said other passage means.

12. The modular drainage apparatus according to claim 11 in which said communication means includes:

a vertically disposed tube within said reservoir having its lower end communicating with said liquid seal chamber and its upper end communicating with said reservoir;

and said tube having a set of holes adjacent its lower end to provide communication between the interior of said tube and said reservoir.

13. The modular drainage apparatus according to claim 1 including:

flexible means means connecting said inlet means to the pleural cavity of the body;

connecting means connecting said flexible means with said collection chamber remote from said inlet means;

and said connecting means including control means to prevent flow of fluid from said flexible means through said connecting means while allowing communication of said flexible means with said collection chamber through said connecting means to maintain a selected area of said flexible means at substantially the same negative pressure as said collection chamber.

14. The modular drainage apparatus according to claim 13 in which said flexible means includes:

a connector having a passage extending therethrough and communicating through said control means with said connecting means so that said passage is the selected area of said flexible means;

a first flexible tube communicating one end of said passage in said connector with the pleural cavity of the body;

and a second flexible tube communicating the other end of said passage in said connector with said inlet means.

15. A modular drainage apparatus including:

three bodies;

each of said bodies including at least one chamber having an upper wall;

each of said bodies having a groove on each side thereof adjacent at least said upper wall of said one chamber;

support means to support each of said bodies;

said support means having a longitudinally extending wall;

said support means having means for disposition within said grooves in each of said bodies to cause each of said bodies to have said upper wall of at least said one chamber abut said longitudinally extending wall of said support means;

said upper wall of said one chamber of each of said bodies having at least one opening therein;

said support means having two passage means;

said longitudinally extending wall of said support means having openings therein to enable at least said one opening in said upper wall of said one chamber of each of said bodies to communicate with one of said passage means of said support means so that said one chamber of each of said bodies communicates with said one chamber of at least one other of said bodies;

a first of said bodies having said one chamber communicating with one of said passage means through said one opening in said upper wall of said one chamber;

a second of said bodies having two openings in said upper wall of said one chamber, said one chamber of said second body communicating with said one passage means through one of said openings to communicate with said one chamber of said first body and said one chamber of said second body communicating with the other of said passage means remote from its communication with said one passage means through the other of said openings;

a third of said bodies having said one chamber communicating with said other passage means through said one opening in said upper wall of said one chamber to communicate with said one chamber of said second body, said one chamber of said third body being a collection chamber having inlet means for connection to a pleural cavity of a body to receive fluids therefrom;

said one chamber of said second body including a liquid seal chamber adapted to have a selected quantity of liquid therein;

said one passage means including means to enable a negative pressure to be applied to said liquid seal chamber and said collection chamber and to remove gases from the fluids in said collection chamber to said liquid seal chamber;

said one chamber of said first body controlling the pressure produced in said liquid seal chamber and said collection chamber;

and said second body having an excess negativity chamber having one end communicating with said other passage means and its other end communicating with the atmosphere and adapted to have a selected quantity of liquid therein to limit the negative pressure within said collection chamber to a selected maximum above the negative pressure controlled by said one chamber of said first body.

16. The modular drainage apparatus according to claim 15 in which:

said one chamber of said first body is a U-shaped regulating chamber having one end exposed to the atmosphere and its other end connected to said one passage means;

and said U-shaped regulating chamber is adapted to have a selected quantity of liquid therein to control the negative pressure produced in said liquid seal chamber and said collection chamber.

17. The modular drainage apparatus according to claim 16 including means to prevent the flow of liquid from said one end of said excess negativity chamber while allowing air to flow through said excess negativity chamber to reduce the negative pressure in said collection chamber.

18. The modular drainage apparatus according to claim 17 in which said longitudinally extending wall of said support means forms the bottom wall of each of said passage means of said support means.

19. The modular drainage apparatus according to claim 18 in which:
said second body includes a reservoir between said other opening in said upper wall of said one chamber and said liquid seal chamber;
communication means provides communication between said reservoir and said liquid seal chamber;
said reservoir provides communication between said excess negativity chamber and said liquid seal chamber and between said excess negativity chamber and said other opening in said upper wall of said one chamber;
and said communication means includes means to prevent the flow of liquid from said liquid seal chamber through said reservoir to said other passage means.

20. The modular drainage apparatus according to claim 19 in which said communication means includes:
a vertically disposed tube within said reservoir having its lower end communicating with said liquid seal chamber and its upper end communicating with said reservoir;
and said tube having a set of holes adjacent its lower end to provide communication between the interior of said tube and said reservoir.

21. The modular drainage apparatus according to claim 16 in which:
said second body includes a reservoir between said other opening in said upper wall of said one chamber and said liquid seal chamber;
communication means provides communication between said reservoir and said liquid seal chamber;
said reservoir provides communication between said excess negativity chamber and said liquid seal chamber and between said excess negativity chamber and said other opening in said upper wall of said one chamber;
and said communication means includes means to prevent the flow of liquid from said liquid seal chamber through said reservoir to said other passage means.

22. The modular drainage apparatus according to claim 21 in which said communication means includes:
a vertically disposed tube within said reservoir having its lower end communicating with said liquid seal chamber and its upper end communicating with said reservoir;
and said tube having a set of holes adjacent its lower end to provide communication between the interior of said tube and said reservoir.

23. The modular drainage apparatus according to claim 15 including means to prevent the flow of liquid from said one end of said excess negativity chamber while allowing air to flow through said excess negativity chamber to reduce the negative pressure in said collection chamber.

24. The modular drainage apparatus according to claim 23 in which said longitudinally extending wall of said support means forms the bottom wall of each of said passage means of said support means.

25. The modular drainage apparatus according to claim 16 in which:
said second body includes a reservoir between said other opening in said upper wall of said one chamber and said liquid seal chamber;
communication means provides communication between said reservoir and said liquid seal chamber;
said reservoir provides communication between said excess negativity chamber and said liquid seal chamber and between said excess negativity chamber and said other opening in said upper wall of said one chamber;
and said communication means includes means to prevent the flow of liquid from said liquid seal chamber through said reservoir to said other passage means.

26. The modular drainage apparatus according to claim 25 in which said communication means includes:
a vertically disposed tube within said reservoir having its lower end communicating with said liquid seal chamber and its upper end communicating with said reservoir;
and said tube having a set of holes adjacent its lower end to provide communication between the interior of said tube and said reservoir.

27. The modular drainage apparatus according to claim 15 in which:
said second body includes a reservoir between said other opening in said upper wall of said one chamber and said liquid seal chamber;
communication means provides communication between said reservoir and said liquid seal chamber;
said reservoir provides communication between said excess negativity chamber and said liquid seal chamber and between said excess negativity chamber and said other opening in said upper wall of said one chamber;
and said communication means includes means to prevent the flow of liquid from said liquid seal chamber through said reservoir to said other passage means.

28. The modular drainage apparatus according to claim 27 in which said communication means includes:
a vertically disposed tube within said reservoir having its lower end communicating with said liquid seal chamber and its upper end communicating with said reservoir;
and said tube having a set of holes adjacent its lower end to provide communication between the interior of said tube and said reservoir.

29. The modular drainage apparatus according to claim 1 in which said excess negativity chamber is separate from said liquid seal chamber and has its other end communicating with the atmosphere independently of said liquid seal chamber.

30. The modular drainage apparatus according to claim 1 including means to control the flow rate of air from the atmosphere through said excess negativity chamber to control the period of time required to limit the excess negative pressure to the selected maximum.

31. The modular drainage apparatus according to claim 15 in which said excess negativity chamber is separate from said liquid seal chamber.

32. The modular drainage apparatus according to claim 15 including means to control the flow rate of air from the atmosphere through said excess negativity chamber to control the period of time required to limit the excess negative pressure to the selected maximum.

33. A modular drainage apparatus including:
three bodies;
each of said bodies including at least one chamber having an upper wall;

each of said bodies having a groove on each side thereof adjacent at least said upper wall of said one chamber;

support means to support each of said bodies;

said support means having a longitudinally extending wall;

said support means having means for disposition within said grooves in each of said bodies for support of each of said bodies;

said upper wall of said one chamber of each of said bodies having at least one opening therein;

said support means having two passage means;

said longitudinally extending wall of said support means having openings therein to enable at least said one opening in said upper wall of said one chamber of each of said bodies to communicate with one of said passage means of said support means so that said one chamber of each of said bodies communicates with said one chamber of at least one other of said bodies;

a first of said bodies having said one chamber communicating with one of said passage means through said one opening in said upper wall of said one chamber;

a second of said bodies having two openings in said upper wall of said one chamber, said one chamber of said second body communicating with said one passage means through one of said openings to communicate with said one chamber of said first body and said one chamber of said second body communicating with the other of said passage means remote from its communication with said one passage means through the other of said openings;

a third of said bodies having said one chamber communicating with said other passage means through said one opening in said upper wall of said one chamber to communicate with said one chamber of said second body, said one chamber of said third body being a collection chamber having inlet means for connection to a pleural cavity of a body to receive fluids therefrom;

said one chamber of said second body including a liquid seal chamber adapted to have a selected quantity of liquid therein;

said one passage means including means to enable a negative pressure to be applied to said liquid seal chamber and said collection chamber and to remove gases from the fluids in said collection chamber to said liquid seal chamber;

said one chamber of said first body controlling the pressure produced in said liquid seal chamber and said collection chamber;

and said second body having an excess negativity chamber having one end communicating with said other passage means and its other end communicating with the atmosphere and adapted to have a selected quantity of liquid therein to limit the negative pressure within said collection chamber to a selected maximum above the negative pressure controlled by said one chamber of said first body.

34. The modular drainage apparatus according to claim 33 in which:

said one chamber of said first body is a U-shaped regulating chamber having one end exposed to the atmosphere and its other end connected to said one passage means;

and said U-shaped regulating chamber is adapted to have a selected quantity of liquid therein to control the negative pressure produced in said liquid seal chamber and said collection chamber.

35. The modular drainage apparatus according to claim 34 including means to control the flow rate of air from the atmosphere through said excess negativity chamber to control the period of time required to limit the excess negative pressure to the selected maximum.

36. The modular drainage apparatus according to claim 35 in which:

said second body includes a reservoir between said other opening in said upper wall of said one chamber and said liquid seal chamber;

communication means provides communication between said reservoir and said liquid seal chamber;

said reservoir provides communication between said excess negativity chamber and said liquid seal chamber and between said excess negativity chamber and said other opening in said upper wall of said one chamber;

and said communication means includes means to prevent the flow of liquid from said liquid seal chamber through said reservoir to said other passage means.

37. The modular drainage apparatus according to claim 36 in which said communication means includes:

a vertically disposed tube within said reservoir having its lower end communicating with said liquid seal chamber and its upper end communicating with said reservoir;

and said tube having means adjacent its lower end to provide communication between the interior of said tube and said reservoir.

38. The modular drainage apparatus according to claim 34 including means to control the flow rate of air from the atmosphere through said excess negativity chamber to control the period of time required to limit the excess negative pressure to the selected maximum.

39. The modular drainage apparatus according to claim 38 in which:

said second body includes a reservoir between said other opening in said upper wall of said one chamber and said liquid seal chamber;

communication means provides communication between said reservoir and said liquid seal chamber;

said reservoir provides communication between said excess negativity chamber and said liquid seal chamber and between said excess negativity chamber and said other opening in said upper wall of said one chamber;

and said communication means includes means to prevent the flow of liquid from said liquid seal chamber through said reservoir to said other passage means.

40. The modular drainage apparatus according to claim 39 in which said communication means includes:

a vertically disposed tube within said reservoir having its lower end communicating with said liquid seal chamber and its upper end communicating with said reservoir;

and said tube having means adjacent its lower end to provide communication between the interior of said tube and said reservoir.

41. The modular drainage apparatus according to claim 33 in which:

said second body includes a reservoir between said other opening in said upper wall of said one chamber and said liquid seal chamber;

communication means provides communication between said reservoir and said liquid seal chamber;

said reservoir provides communication between said excess negativity chamber and said liquid seal chamber and between said excess negativity chamber and said other opening in said upper wall of said one chamber;

and said communication means includes means to prevent the flow of liquid from said liquid seal chamber through said reservoir to said other passage means.

42. The modular drainage apparatus according to claim 41 in which said communication means includes:

a vertically disposed tube within said reservoir having its lower end communicating with said liquid seal chamber and its upper end communicating with said reservoir;

and said tube having means adjacent its lower end to provide communication between the interior of said tube and said reservoir.

43. The modular drainage apparatus according to claim 33 in which said excess negativity chamber is separate from said liquid seal chamber.

* * * * *

UNITED STATES PATENT AND TRADEMARK OFFICE
CERTIFICATE OF CORRECTION

PATENT NO. : 4,534,765

DATED : August 13, 1985

INVENTOR(S) : Edward P. Todd et al

It is certified that error appears in the above-identified patent and that said Letters Patent is hereby corrected as shown below:

Title Block: "Assignee: Snyder Laboratories, Inc., Dover, Ohio" should read --- Assignee: Eugene E. Weilbacher to Snyder Laboratories, Inc., Dover, Ohio ---.

Column 1, line 12, before "there" insert a --- comma (,) ---.

Column 8, line 61, "1" should read --- 1) ---.

Column 19, line 30, "16" should read --- 17 ---.

Signed and Sealed this

Nineteenth Day of November 1985

[SEAL]

Attest:

Attesting Officer

DONALD J. QUIGG

Commissioner of Patents and Trademarks